US012678188B2

(12) United States Patent (10) Patent No.: US 12,678,188 B2
Olsen et al. (45) Date of Patent: Jul. 14, 2026

(54) LOOP DISSECTOR

(71) Applicant: EyeMacular Regeneration, Inc., St. Paul, MN (US)

(72) Inventors: Timothy W. Olsen, Rochester, MN (US); Antonio Joao Ubach, Tucson, AZ (US); Mikhail Borisovich Tikh, St. Louis Park, MN (US)

(73) Assignee: EyeMacular Regeneration, Inc., St. Paul, MN (US)

( * ) Notice: Subject to any disclaimer, the term of this patent is extended or adjusted under 35 U.S.C. 154(b) by 0 days.

(21) Appl. No.: 18/620,316

(22) Filed: Mar. 28, 2024

(65) Prior Publication Data

US 2025/0302500 A1      Oct. 2, 2025

(51) Int. Cl.
A61B 17/3205 (2006.01)
A61B 17/00 (2006.01)
A61B 17/32 (2006.01)

(52) U.S. Cl.
CPC .................. A61B 17/32056 (2013.01); A61B 2017/00867 (2013.01); A61B 2017/320044 (2013.01)

(58) Field of Classification Search
CPC ...... A61B 17/00234; A61B 17/320016; A61B 2017/00292; A61B 2017/00778; A61B 2017/00783; A61B 2017/320044
See application file for complete search history.

(56) References Cited

U.S. PATENT DOCUMENTS 5,486,183 A * 1/1996 Middleman ...... A61B 17/32056
606/127
5,601,572 A 2/1997 Middleman et al.
5,860,987 A * 1/1999 Ratcliff .............. A61B 17/0218
606/113
10,631,893 B2 4/2020 Drapeau et al.
11,160,935 B2 11/2021 Scheller et al.
11,166,844 B2 11/2021 Charles
11,490,915 B2 11/2022 Abt et al.
2007/0005093 A1* 1/2007 Cox ........................ A61B 90/30
606/198
2009/0275970 A1* 11/2009 Leibowitz .......... A61B 17/3496
606/185

OTHER PUBLICATIONS

"International Application Serial No. PCT US2025 021350, International Search Report mailed May 16, 2025", 4 pgs.
"International Application Serial No. PCT US2025 021350, Written Opinion mailed May 16, 2025", 7 pgs.

* cited by examiner

*Primary Examiner* — Tuan V Nguyen
(74) *Attorney, Agent, or Firm* — Schwegman Lundberg & Woessner, P.A.

(57) ABSTRACT

A device includes a tube and a filament. The tube has a first end, a second end, and a center axis disposed between the first end and the second end. The filament is disposed at the first end and having a portion configured as a loop aligned on an extension of a lumen of the tubular segment. A portion of the filament is configured for axial movement within the lumen.

22 Claims, 13 Drawing Sheets

LOOP DISSECTOR

TECHNICAL FIELD

This document pertains generally, but not by way of limitation, to a surgical instrument.

BACKGROUND

A surgical procedure, such as implantation of a medical device at a tissue site, can include preparing a void or a cavity into which the device can be placed. One such procedure can include blunt dissection which entails separating tissue planes in a manner not requiring cutting using a sharpened edge. Some large-scale blunt dissection procedures can be performed by manipulating fingers in the tissue to form a suitable cavity. For smaller dimensions, the fingers of a surgeon do not allow for precise formation of a small cavity.

SUMMARY

The present inventor has recognized, among other things, that a problem to be solved can include forming a small-dimension cavity at a tissue site. The present subject matter can help provide a solution to this problem, such as by a manually operable device having a controllable blunt dissection loop having elasticity in certain dimensions, appropriate angulation, and rigidity in other dimensions and having a loop cross section configured for precise cavity size and configuration.

An example of the present subject matter can be deployed to form a cavity of a particular dimension and location suited to a surgical procedure. Imprecision in dimensions and placement can lead to improper placement or unwanted device migration.

An example includes a tube having a filament in which a portion of the filament is carried within a lumen of the tube and controlled by filament guides to reduce torsion. The filament is configured for axial movement. When unrestrained by the tube, the filament is configured to take a loop form. An edge of the loop is blunted or rounded in a manner to enable blunt dissection of tissue at the tissue site.

An example of the present subject matter provides good conformation of the dissection space using a blunt dissection device of similar shape and size. Good congruence between the dissection space and the implanted device provides a fit that ensures the device does not migrate.

Each of these non-limiting examples can stand on its own, or can be combined in various permutations or combinations with one or more of the other examples.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
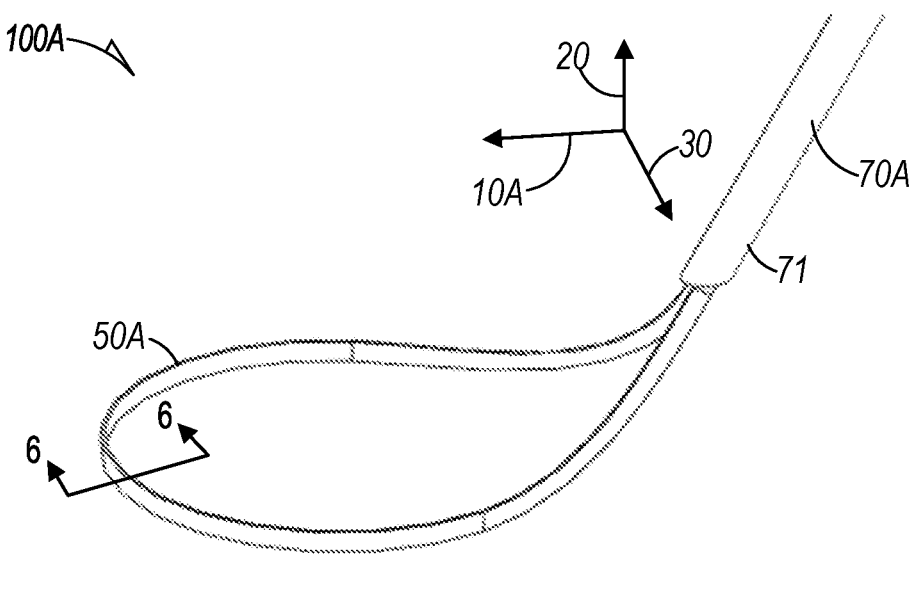
FIGS. 1A, 1B, and 1C include views of a device according to one example.
Figure 1B:
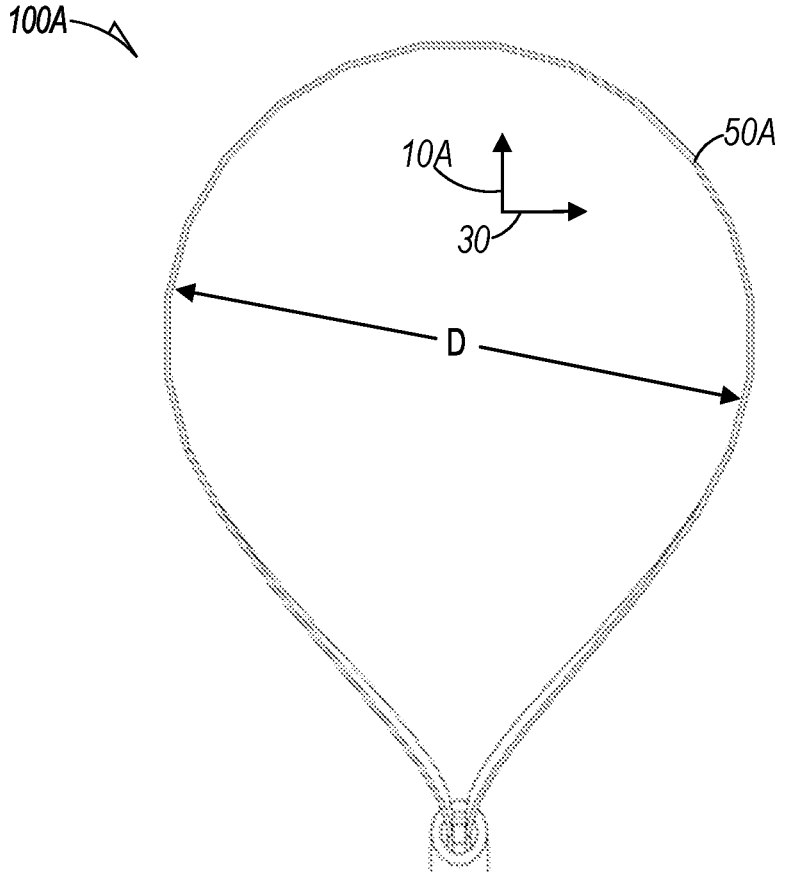
Figure 1C:
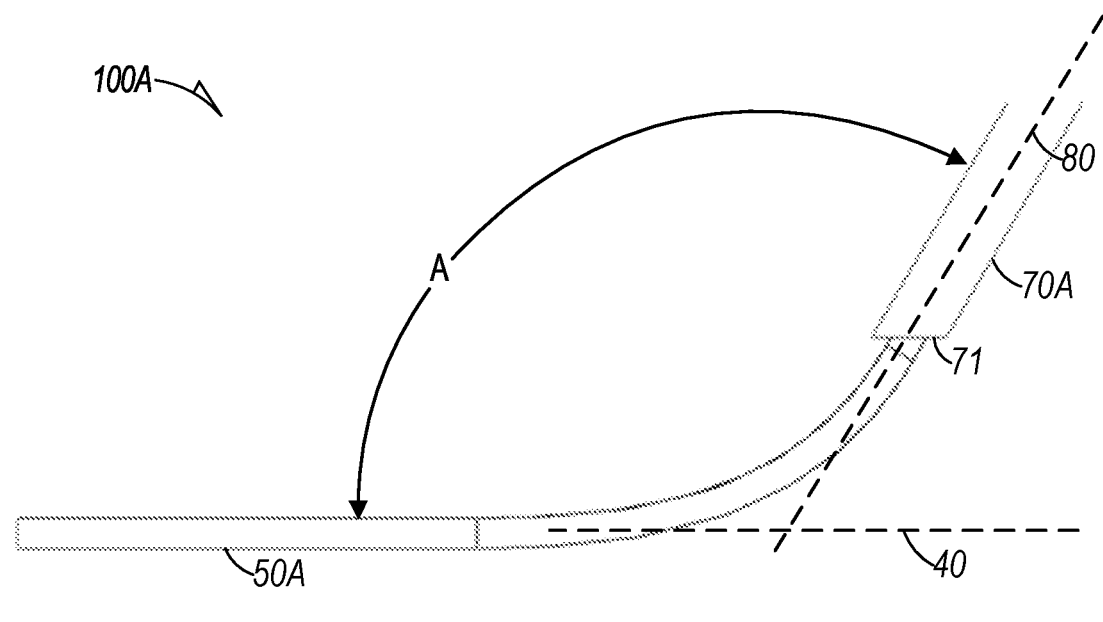

FIGS. 1A, 1B, and 1C include views of device 100A according to one example. FIGS. 1A, 1B, and 1C depict a perspective view, a top view, and a side view, respectively, of a portion of device 100A. FIG. Device 100A includes tube 70A aligned on axis 80. Axis 80 is coaxial with the lumen of tube 70A.

In the example shown, filament 50A includes filament ends that pass into the lumen of tube 70A at end 71 resulting in filament 50A taking on the shape of a noose. Filament 50A, in the example shown, has a ribbon or band form when viewed in cross section at 5-5.

The view in FIG. 1B illustrates a measure of diameter dimension D. In one example, dimension D is approximately 3 mm.

The view in FIG. 1C illustrates alignment of axis 80 and axis 40. Axis 80 is coaxial with tube 70A. Axis 40 lies in a plane parallel to a substantial portion of filament 50A. In the example shown, axis 80 and axis 40 are at an angle A of 120 degrees. Filament movement along axis 80 (within a certain range) relative to tube 70A causes the plane denoted by axis 40 to raise and lower without a change in angle A. On the other hand, for some filament movement along axis 80, relative to tube 70A, the plane denoted by axis 40 undergoes a change in angle A. Namely, as the end of filament 50A is retracted into the lumen of tube 70A, angle A increases to approximately 180 degrees. Angle A can be a right angle, oblique, or obtuse.

In this manner, filament 50A can be manipulated to a selected deployment dimension and thus to a selected angular deflection. Accordingly, with a small dimension of deployment, filament 50A lies in a plane at a shallow angle relative to the axis 80 and with a larger dimension of deployment, filament 50A lies in a plane at a greater angle, such as 120 degrees.

A user can manipulate device 100A by moving in a forward direction as indicated at arrow 10A, in a sideways movement as indicated at arrow 30, and in an upward direction as indicated by arrow 20. Manipulating device 100A to cause movement in these directions (and in opposite directions) can be effective to displace tissue at a tissue site and thereby form a cavity or pocket to receive an implantable device. The movement of filament 50, within the tissue at the tissue site, can facilitate blunt dissection of the tissue.

Figure 2A:
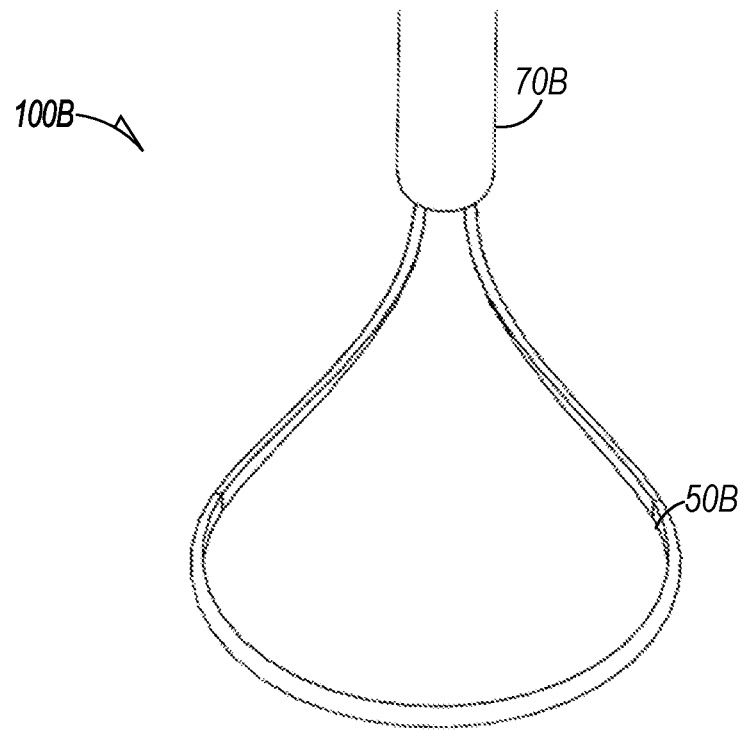
FIGS. 2A and 2B include views of a device according to one example.
Figure 2B:
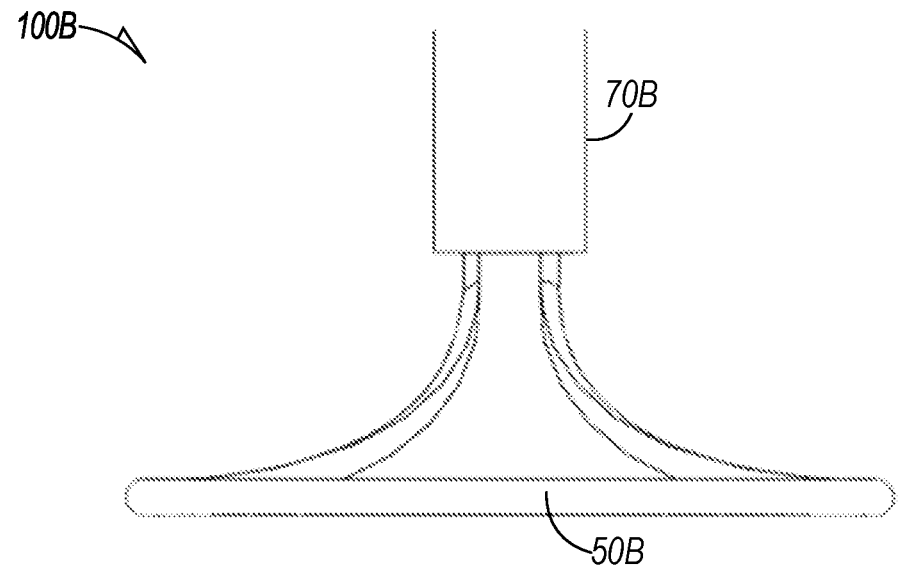

FIGS. 2A and 2B include views of device 100B according to one example. Device 100B, as shown in FIG. 2A, includes tube 70B and filament 50B. Filament 50B includes a semicircular cross section. A rounded portion of the cross section lies on an outer surface of the loop and a flat portion of the cross section lies on an inner surface of the loop. As shown in the view of FIG. 2B, a substantial portion of filament 50B lies in a plane and a portion of filament 50B is curved in a manner to align with a lumen of tube 70B. Both the first and second end of filament 50B are shown to pass into the lumen of tube 70B in this example.

Figure 3A:
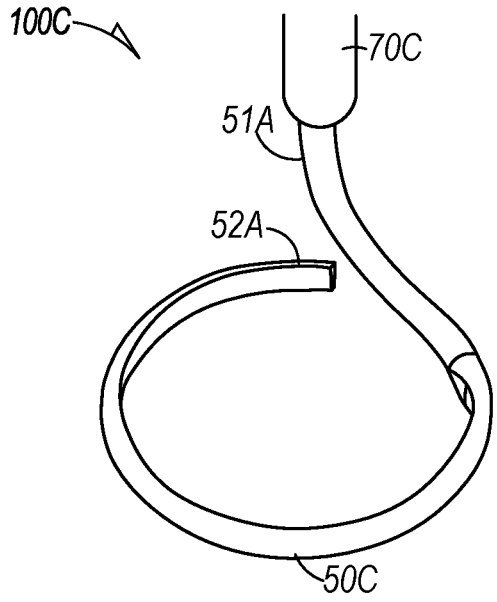
FIGS. 3A and 3B include views of a device according to one example.
Figure 3B:
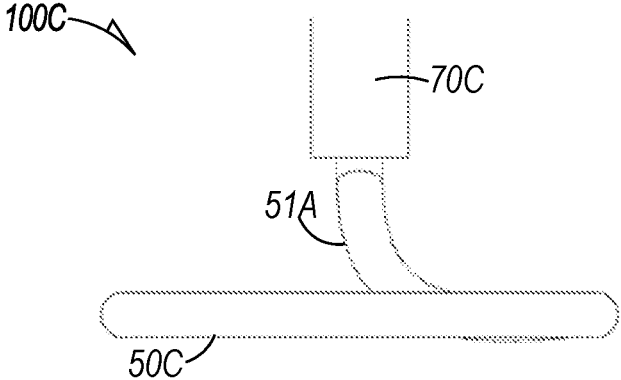

FIGS. 3A and 3B include views of device 100C according to one example. Device 100C, as shown in FIG. 3A, includes tube 70C and filament 50C. Filament 50C includes a substantially circular cross section. As shown in the view of FIG. 3B, a substantial portion of filament 50C lies in a plane and a portion of filament 50C is curved in a manner to align with a lumen of tube 70C. As shown, first end 51A of filament 50C is shown to pass into the lumen of tube 70C and second end 52A of filament 50C is shown to be clear of the lumen of tube 70C. Second end 52A is spaced apart from a portion of filament 50C by a small gap.

Figure 4A:
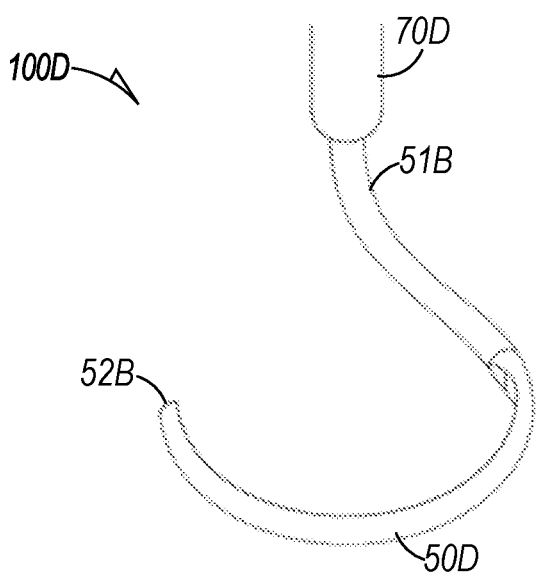
FIGS. 4A and 4B include views of a device according to one example.
Figure 4B:
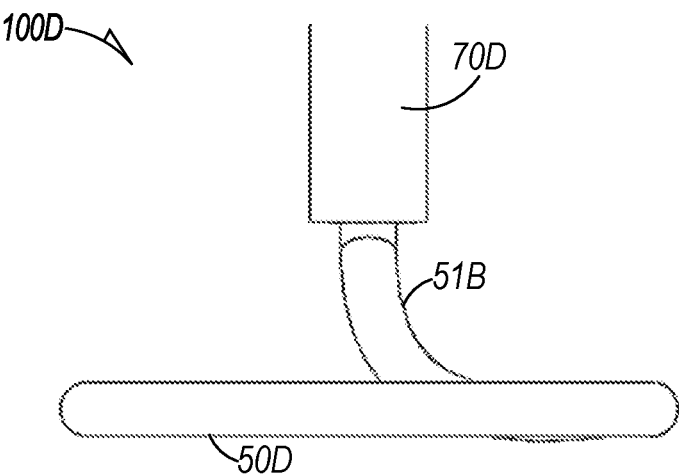

FIGS. 4A and 4B include views of device 100D according to one example. Device 100D, as shown in FIG. 4A, includes tube 70D and filament 50D. Filament 50D includes a substantially circular cross section. As shown in the view of FIG. 4B, a substantial portion of filament 50D lies in a plane and a portion of filament 50D is curved in a manner to align with a lumen of tube 70D. As shown, first end 51B of filament 50D is shown to pass into the lumen of tube 70D and second end 52B of filament 50D is shown to be clear of the lumen of tube 70D. Second end 52B is spaced apart from a portion of filament 50D by a relatively large gap.

Figure 5D:
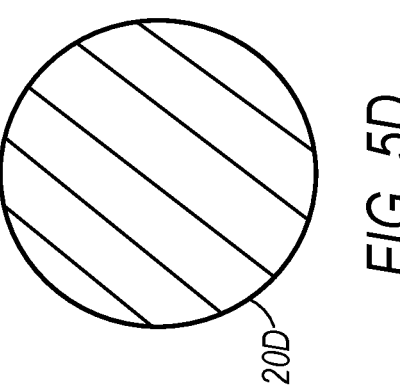
FIGS. 5A, 5B, 5C, and 5D include cross section views of devices, according to various examples.
Figure 5C:
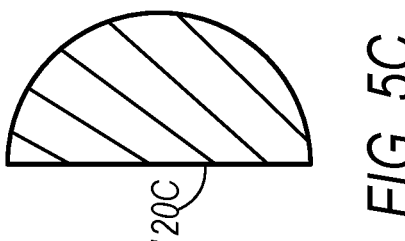
Figure 5B:
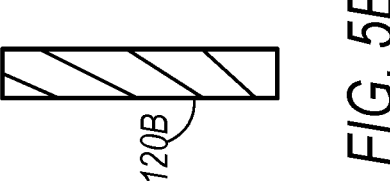
Figure 5A:
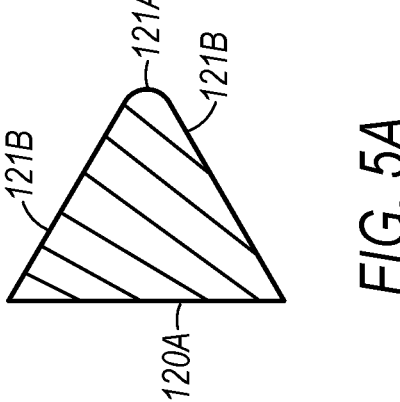

FIGS. 5A, 5B, 5C, and 5D include selected cross section views of a filament for providing blunt dissection, according to various examples. The examples shown in FIGS. 5A, 5B, 5C, and 5D can be understood to depict a view at section line 5-5 of FIG. 1A. In FIG. 5A, for example, cross section 120A depicts a substantially triangular profile having apex 121A and flanks 121B. A radius at apex 121A can be selected to ease blunt dissection without cutting tissue in a particular lamella. In FIG. 5B, for example, cross section 120B depicts a substantially rectangular profile. Cross section 120B can be described as a band or ribbon. The dimensions of a filament, such as that according to the example of FIG. 5B, can be selected to provide blunt dissection. In FIG. 5C, for example, cross section 120C depicts a semicircular profile. The dimensions of a filament according to the example of FIG. 5C can be selected to provide dissection. The semicircular profile can be more than, or less than, a half circle. In FIG. 5D, for example, cross section 120D depicts a circular profile. This example can represent a cord, wire, or braided cable. The dimensions of a filament according to the example of FIG. 5D can be selected to provide blunt dissection. Other examples are also contemplated.

Figure 6:
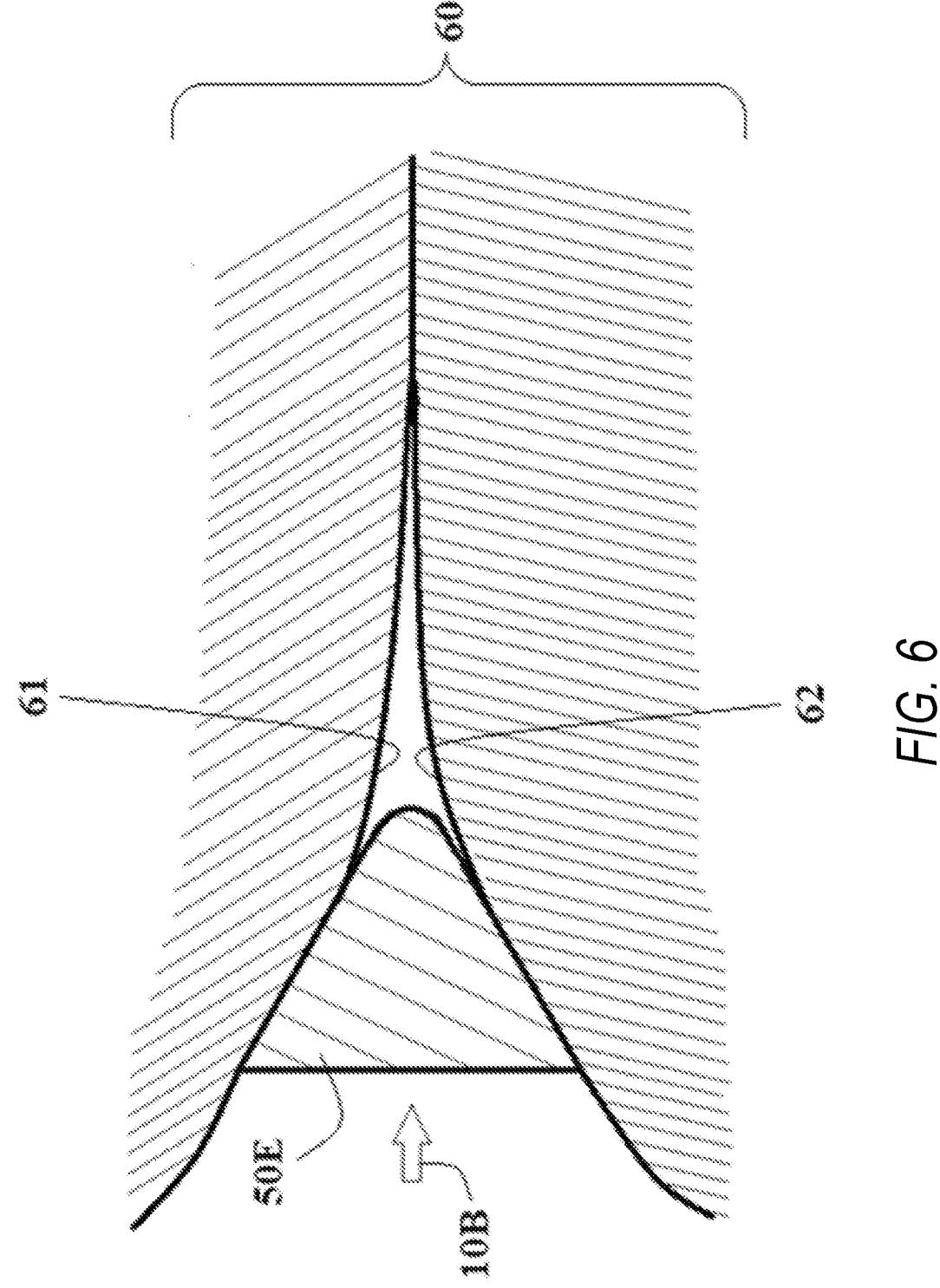
FIG. 6 includes a view of a device and tissue in according to one example.

FIG. 6 includes a view of a device having filament 50E as shown in FIG. 5A and tissue in accordance to one example. As shown, filament 50E can be manipulated to separate tissue lamella 61 and tissue lamella 62 with a force exerted in a direction indicated by arrow 10B. In this manner, the apex of filament 50E separates tissue 60 without cutting at a sharp edge and facilitates formation of a cavity into which an implantable device can be positioned. Filament 50E can be manipulated in pulses as indicated in the direction of arrow 10B or in pulses, in a lateral motion that includes FIG. 1A such as 10A, 20, or 30, or in other directions or combinations of directions.

By way of example, tissue 60 can include hydrologically connected tissue lamella. The tissue can be opened or separated in a manner to form a pocket for receiving an implantable device.

Figure 7A:
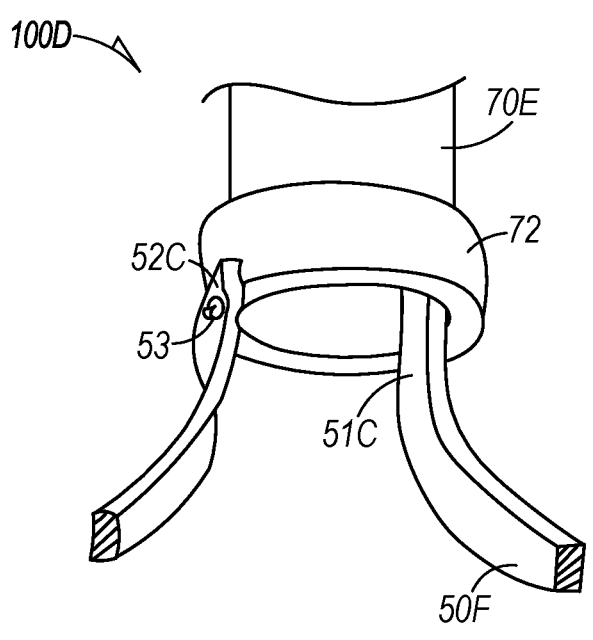
FIGS. 7A and 7B include views of a device according to one example.
Figure 7B:
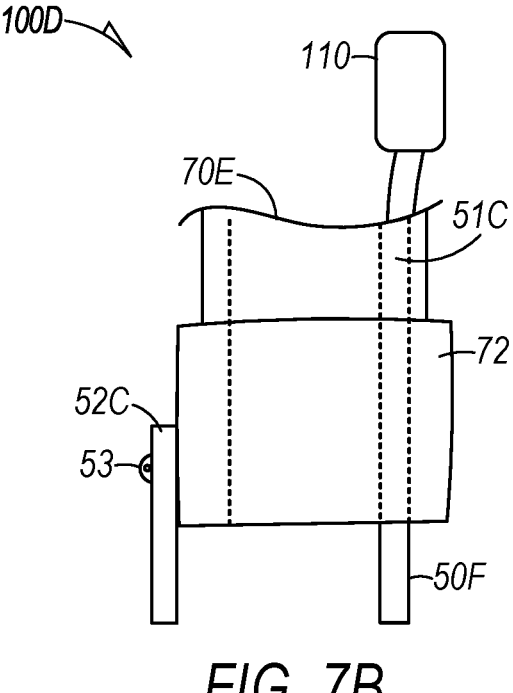

FIGS. 7A and 7B include views of device 100D according to one example. FIG. 7A depicts a perspective view showing tube 70E terminated with ferrule 72. A lumen of tube 70E provides passage for first end 51C of filament 50F. Second end 52C of filament 50F is affixed to ferrule 72 (and thus attached to tube 70E) by fastener 53. In the example shown, second end 52C is affixed to an outer surface of ferrule 72 and in other examples, second end 52C is affixed to tube 70E (or ferrule 72) by means of attachment at other locations, such as at an interior of ferrule 72. Fastener 53 can include a screw, a pin, a rivet, or other means of coupling end 52C in a fixed position relative to tube 70E. FIG. 7A depicts a portion of filament 50F as denoted by the section lines.

FIG. 7B depicts a profile view of device 100D. As shown, first end 51C of filament 50F passes through the lumen of ferrule 72 and the lumen of tube 70E and is coupled to actuator 110. Actuator 110 can include a finger-manipulated slider or plunger assembly. An external force applied to actuator 110 induces motion of a portion of filament 50F in an axial direction relative to tube 70E. Second end 52C of filament 50F is affixed to ferrule 72 by fastener 53.

In one example both the first end and the second end of a filament are coupled to actuator 110. Manipulation of actuator 110, in such an example, induces axial movement of the filament ends within a lumen of the tube.

Figure 8:
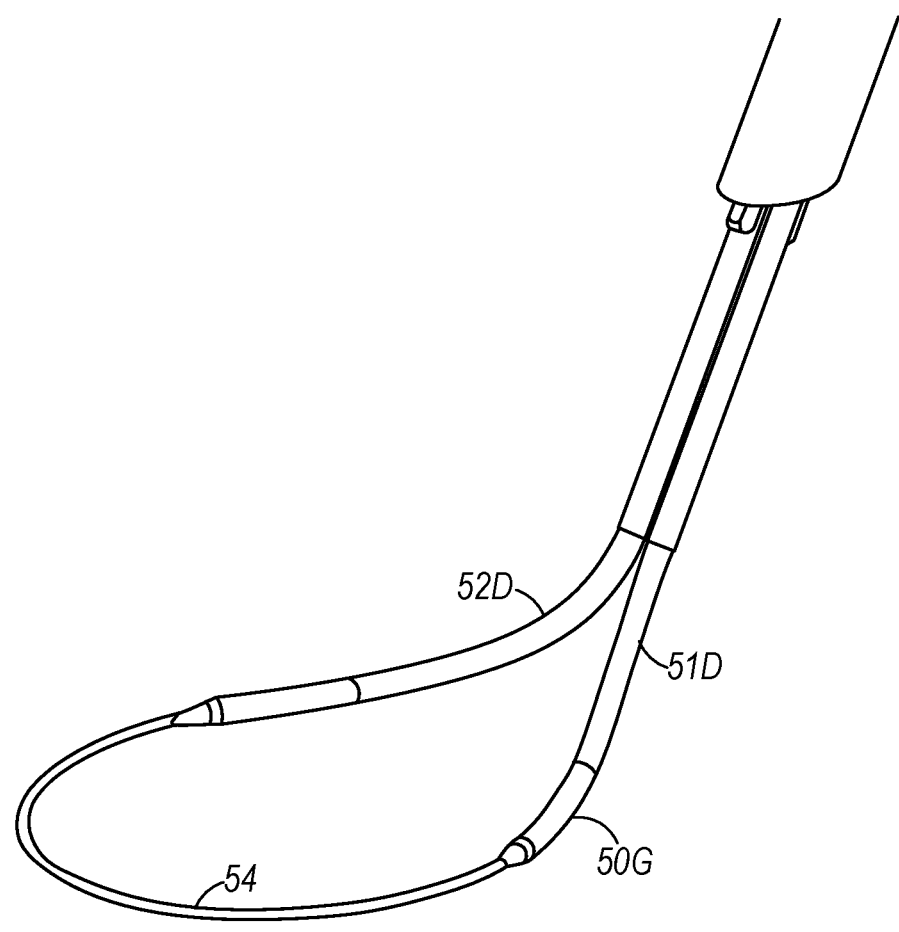
FIG. 8 includes a view of a filament according to one example.

FIG. 8 includes a view of filament 50G according to one example. In the figure, first end 51D and second end 52D have a round cross section of a selected diameter. At portion 54, filament 50G has a diameter that differs from first end 51D and second end 52D. The diameter of portion 54 can be less than that of the diameter of first end 51D and second end 52D. Filament 50G, in the example shown, includes tapered portions that transition between a first diameter and a second diameter. The dimensions, materials, and configuration of filament 50G can be selected to achieve a particular flexibility (elasticity or rigidity) or other property suited for a specific purpose in forming a cavity by blunt dissection.

Figure 9:
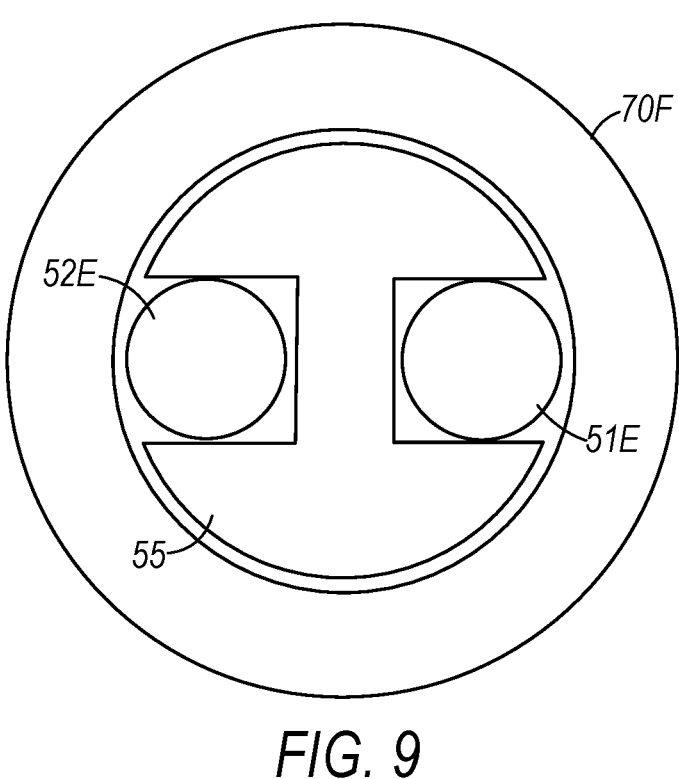
FIG. 9 includes a view of a tube and a filament according to one example.

FIG. 9 includes a view of tube 70F and filament having first end 51E and second end 52E, according to one example. The view depicted is axial with respect to tube 70F and illustrates internal guide 55 disposed in a lumen of tube 70F. Guide 55 provides radially disposed channels that maintain alignment of the filament and preclude twisting or flexing in unintended directions. Guide 55 can have a length suited to ensure desired alignment and as such, can be disposed wholly within a portion of the length of tube 70F or can be disposed in a manner to extend beyond an end of tube 70F. As noted elsewhere in this document, the filament can have a round cross section, rectangular cross section, or other cross section and the channels of guide 55 can be configured to accommodate such sections. Guide 55 can be configured to maintain untwisted alignment of first end 51E and second end 52E and resist helical twisting.

Figure 10:
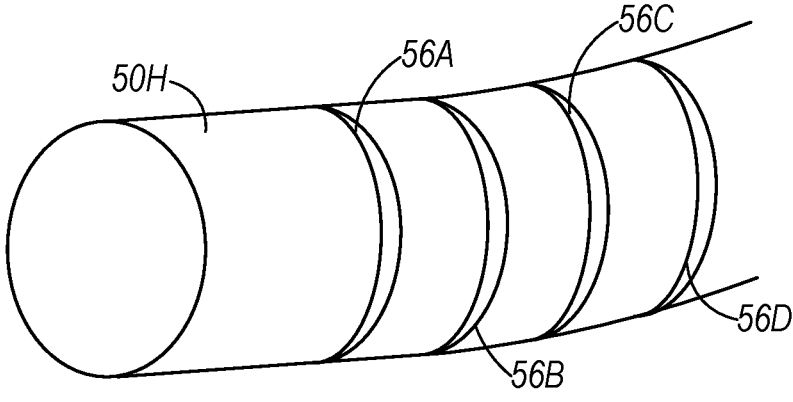
FIG. 10 includes a view of a segment of filament according to one example.

FIG. 10 includes a view of a segment of filament 50H according to one example. In this view, filament 50H includes a round cross section and having axially disposed voids 56A, 56B, 56C, and 56D. Voids 56A, 56B, 56C, and 56D can include a wedge-shaped portion, cut-segments, or scoring configured in a manner to provide increased flexibility in a selected direction. Voids 56A, 56B, 56C, and 56D can facilitate manipulating filament 50H relative to a tube. Other features can be provided as well in order to reduce stress on the filament and reduce incidence of damage or breakage and reduce or mitigate deformation. In this manner, filament 50H can be configured to exhibit hinge-like behavior.

Figure 11A:
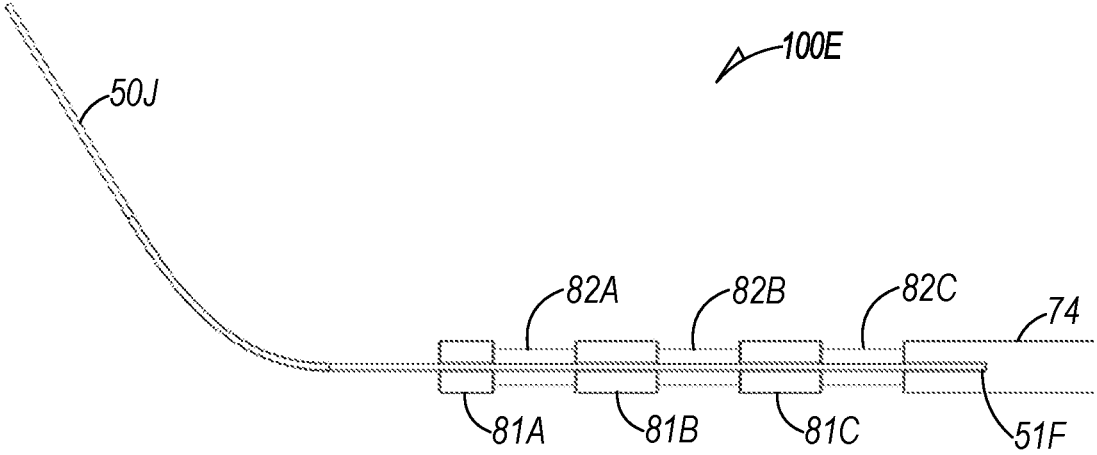
FIGS. 11A, 11B, and 11C illustrate views of a dissector according to one example.
Figure 11B:
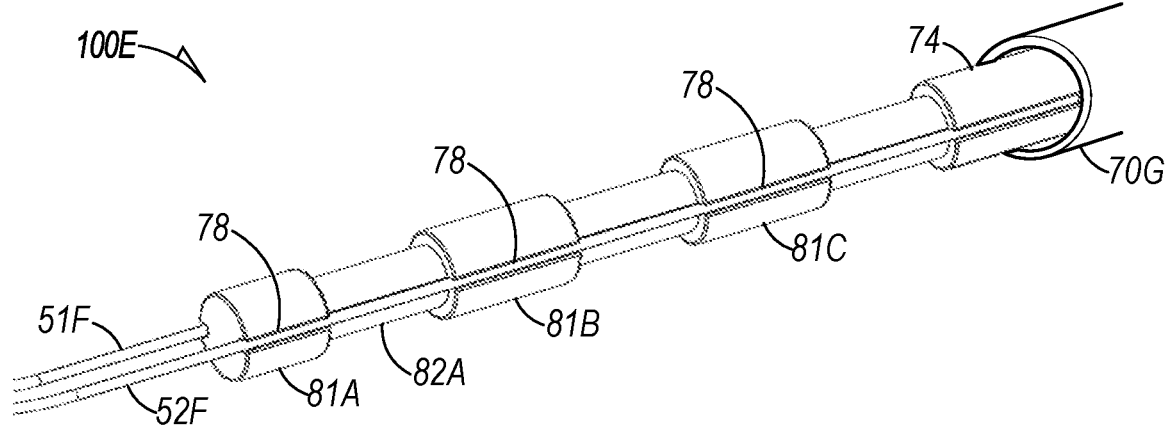
Figure 11C:
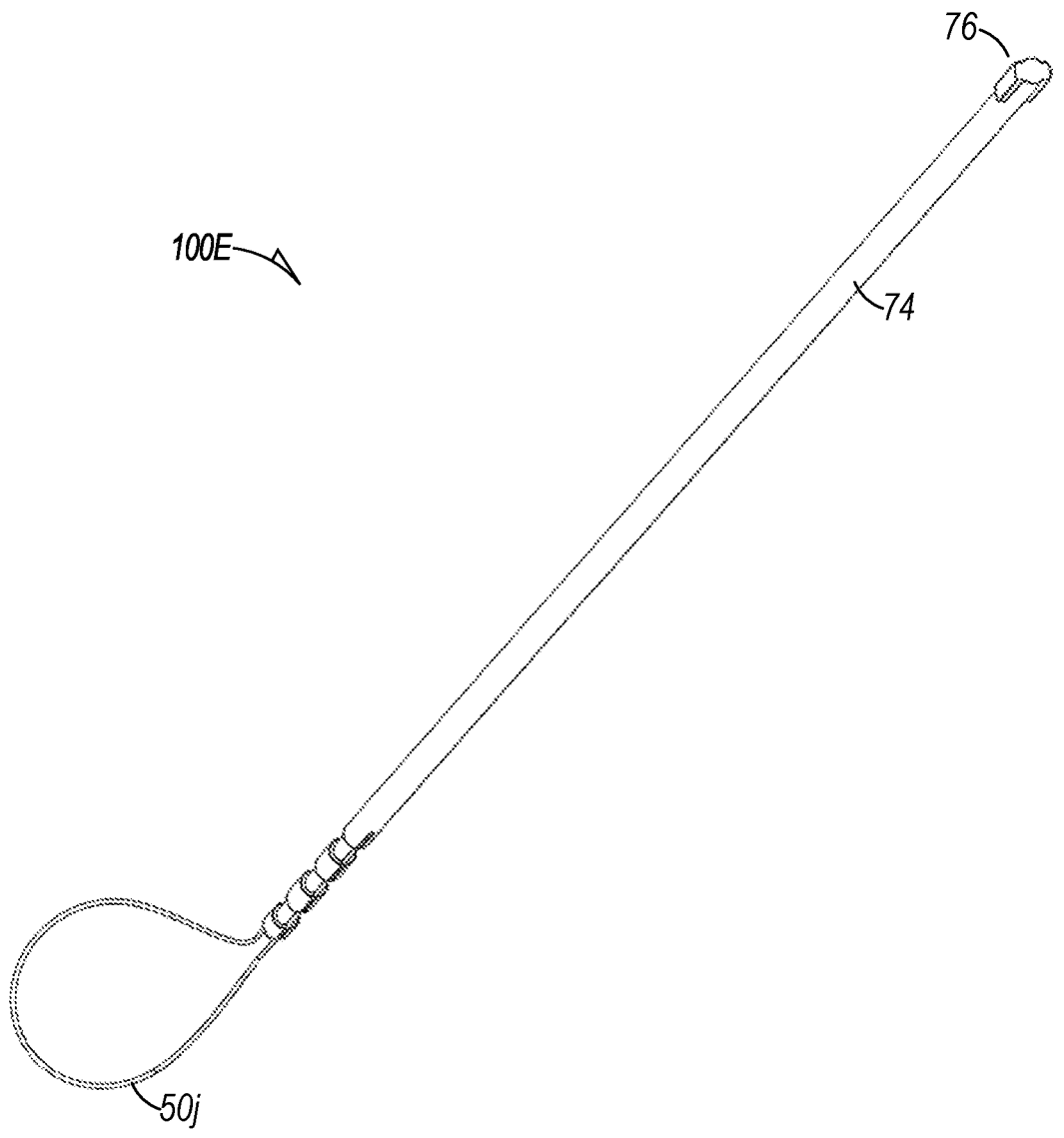

FIGS. 11A, 11B, and 11C illustrate views of device 100E according to one example. In the figures, device 100E includes a filament 50J affixed to rigid shaft 74. In the example shown, shaft 74 includes a stepped segments in which segment 81A, 81B, and 81C have a diameter larger than that of segments 82A, 82B, and 82C. First end 51F is fixedly coupled to shaft 74 by swaged joint 78 at segments 81A, 81B, and 81C. The segments can have rounded edges or tapered faces to facilitate manipulation relative to tube 70G. Swaged joint 78 includes a longitudinal slot configured to receive first end 51F and through a mechanical process of metal forming, in which a dimension of the slot width is reduced, the first end 51F is joined to shaft 74. In the example shown, swaged joints are formed in which both the first end 51F and the second end 52F are coupled to shaft 74 at the selected segments. In the example shown, swaged joints are provided at each of three segments, however, other numbers of swaged joints are also contemplated. Other manners of joining filament 50J to shaft 74, in addition to swaged joints, are also contemplated, including soldering, welding, and an adhesive bond. In one example, filament 50J includes a wire having a diameter of 50 μm.

Shaft 74 is configured for axial movement within a lumen of rigid tube 70G. End connector 76 is affixed to an end of shaft 74 and can include a flange or other coupling to engage with a hand-operated tool by which shaft 74 can be axially positioned within tube 70G.

In the example shown, filament 50J is joined to shaft 74 in a manner that resists twisting. Filament 50J can be drawn into the lumen of tube 70G by pulling on end connector 76 and can be ejected by exerting a pushing force on end connector 76. When drawn into the lumen of tube 70G, filament 50J lies along the longitudinal axis of tube 70G. When free of the lumen of tube 70G, a portion of filament 50J lies at an oblique angle relative to the longitudinal axis of tube 70G, as shown in FIGS. 11A and 11C. In one example, the angle is approximately 120 degrees.

Figure 12:
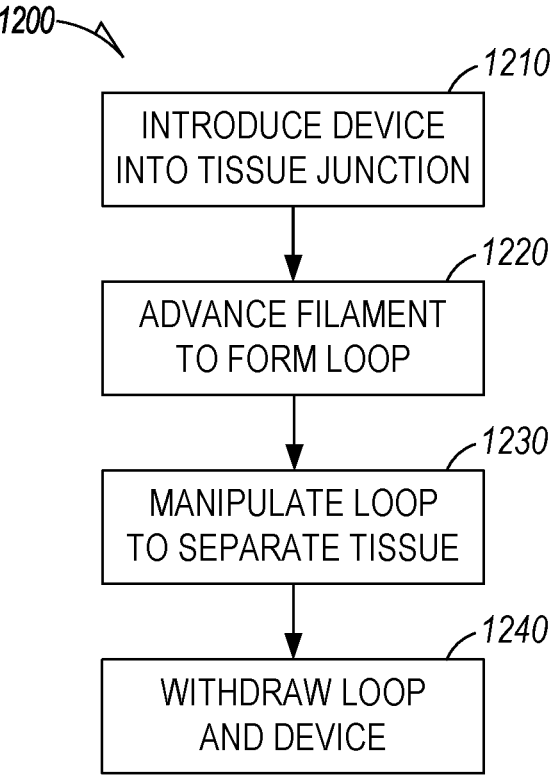
FIG. 12 includes a flowchart of a method according to one example.

FIG. 12 includes a flowchart of method 1200 according to one example. At 1210, the device is introduced into a tissue junction. The tissue junction can include an interface between parallel or adjacent layers of tissue at a tissue site. Access to the tissue junction can be via an aperture or opening, and in one example the device is introduced via a cannula.

At 1220, method 1200 includes advancing a filament to form a loop. In an initial configuration, the filament can be carried, partially or wholly, within a lumen of a tube of the device. The filament can be deployed or ejected from the lumen in response to a force exerted on an actuator coupled to a portion of the filament. Upon emergence from the lumen, the filament expands to a curved, or looped configuration. In the looped configuration, the filament exhibits rigidity when deflected in a first direction (generally normal to a plane of the loop) and exhibits flexibility when deflected in a second direction (generally within a plane of the loop).

At 1230, method 1200 includes manipulating the loop of filament in a direction to separate tissue at the tissue site. Manipulating can include pulsed or continuous force exerted against the junction of tissue lamella. Manipulating proceeds to form a void or cavity of sufficient size at the tissue site. The size of the void can be selected based on the dimensions of the implant device.

At 1240, method 1200 includes withdrawing the device, along with the loop of filament, from the tissue site. This can include extracting the filament through a cannula.

Various Notes

Tube 70A can be configured as a handle or tube 70A can be coupled to a handle. The handle can carry the actuator coupled to the filament.

The filament can be configured to have edges that are blunted or rounded to reduce or eliminate tissue cutting. In various examples, this can entail forming an electropolished finish or deburring.

In various example, the filament is configured to separate tissue without cutting. The filament can include a round section in the form of a wire loop. In one example, the filament includes a thin, elongate membrane having an edge configured for blunt dissection.

A filament can include a shape memory material. In one example, the filament include nitinol configured to have a first configuration at a first temperature and have a second configuration at a second temperature different than the first temperature.

A filament can include a non-shape memory material. In one example, the filament include stainless steel, titanium, or other alloy configured to have elasticity to allow the filament to deflect under moderate force and when free of external force, return to a configuration in which a portion of the filament lies at an oblique angle relative to a longitudinal axis associated with a handle component.

Selected portions of the instant subject matter can be fabricated of various materials. For example, a filament can be fabricated of stainless steel, carbon fiber, a polymer, or other materials and in some examples, includes laminations, wound or woven structure, or coaxial assemblies having layers selected to achieve a particular mechanical property. In addition, the tube can be fabricated of stainless steel, carbon fiber, a polymer, or other materials as well.

In one example, the filament is sized to have dimensions smaller than the finished size of the cavity. In this manner, the user can manipulate the device to expand the cavity dimensions to receive the implant and hold the device in a fixed position. In one example, the device is configured for passage through a cannula of 23 gauge (nominal dimension of 0.6414 mm diameter).

This description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplate examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

This description is intended to be illustrative, and not restrictive. For example, the described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A device for blunt dissection of a tissue comprising:
a tube having a first end, a second end, and a center axis disposed between the first end and the second end; and
a filament disposed at the first end and having a portion configured as a loop aligned on an extension of a lumen of the tube, wherein a portion of the filament is configured for axial movement within the lumen, wherein the loop has an edge that is blunt for the blunt dissection of the tissue;
wherein the filament lies substantially in a plane, and wherein the plane is disposed at an oblique angle relative to the center axis; and wherein the axial movement of the filament along the center axis relative to the tube causes the plane to raise and lower without a change in the oblique angle.

2. The device of claim 1 wherein the filament includes a band.

3. The device of claim 1 wherein the filament includes a metal.

4. The device of claim 1 wherein the filament has a triangular shape in cross-section with the edge formed by an apex of the triangular shape, wherein the apex has a radius.

5. The device of claim 1 wherein the edge is a rounded edge.

6. The device of claim 1 wherein the filament includes a round cross section.

7. The device of claim 1 wherein the filament is flexible.

8. The device of claim 1 wherein the filament includes a shape memory material.

9. The device of claim 1 wherein the portion includes a first segment and a second segment and wherein the first segment is at an obtuse angle relative to the second segment.

10. The device of claim 1 wherein the second end is coupled to a manual actuator tool.

11. The device of claim 1 wherein the filament has an end coupled to a manual actuator tool.

12. The device of claim 1 wherein the first end includes a ferrule.

13. The device of claim 1 wherein the tube includes a handle.

14. A device for blunt dissection of a tissue comprising:
a tube having a lumen on a longitudinal axis;
a filament having a first end and a second end separated by a segment and configured for movement in a first direction aligned parallel with the longitudinal axis and at least a first portion of the filament disposed in the lumen; and
wherein the segment is clear of the lumen and configured as a loop;
wherein the segment for the loop has an edge that is blunt for the blunt dissection of the tissue; and
wherein elasticity of the filament in a second direction aligned parallel to a plane of the segment is less than elasticity of the filament in a third direction aligned normal to the plane.

15. The device of claim 14 wherein the first end is configured for movement in the first direction.

16. The device of claim 14 wherein the second end is clear of the lumen.

17. The device of claim 14 wherein the second end is disposed in the lumen.

18. The device of claim 14 wherein the second end is affixed to the tube.

19. The device of claim 14 wherein the filament includes a band.

20. The device of claim 14 wherein the filament includes a semi-circular section.

21. The device of claim 14 wherein the segment is curved.

22. The device of claim 14 wherein the segment lies substantially in a plane.

* * * * *